United States Patent
Heeren et al.

(10) Patent No.: US 11,051,978 B2
(45) Date of Patent: Jul. 6, 2021

(54) AUTOMATED ASPIRATION THROTTLING IN VITREORETINAL SURGERY

(71) Applicant: Novartis AG, Basel (CH)

(72) Inventors: Tammo Heeren, Aliso Viejo, CA (US); Andrew David Johnson, Laguna Niguel, CA (US)

(73) Assignee: Alcon Inc., Fribourg (CH)

( * ) Notice: Subject to any disclaimer, the term of this patent is extended or adjusted under 35 U.S.C. 154(b) by 427 days.

(21) Appl. No.: 15/590,084

(22) Filed: May 9, 2017

(65) Prior Publication Data

US 2017/0326000 A1  Nov. 16, 2017

Related U.S. Application Data (60) Provisional application No. 62/333,928, filed on May 10, 2016.

(51) Int. Cl.
*A61F 9/007*  (2006.01)
*A61M 3/02*  (2006.01)
*A61M 1/00*  (2006.01)

(52) U.S. Cl.
CPC ....... *A61F 9/00736* (2013.01); *A61M 1/0031* (2013.01); *A61M 1/0058* (2013.01); *A61M 3/022* (2014.02); *A61M 3/0208* (2014.02); *A61M 3/0212* (2014.02); *A61M 3/0216* (2014.02); *A61M 3/0258* (2013.01); *A61M 3/0283* (2013.01); *A61M 2205/078* (2013.01); *A61M 2205/3334* (2013.01); *A61M 2205/3344* (2013.01); *A61M 2205/50* (2013.01); *A61M 2205/52* (2013.01); *A61M 2210/0612* (2013.01)

(58) Field of Classification Search
CPC ............ A61F 9/00736; A61M 1/0076; A61M 3/0283; A61M 2205/52; A61M 2205/50; A61M 2205/3344; A61M 2205/078; A61M 2205/3334
See application file for complete search history.

(56) References Cited

U.S. PATENT DOCUMENTS

| | | | |
|---|---|---|---|
| 4,722,350 A | 2/1988 | Armeniades et al. | |
| 4,841,984 A | * 6/1989 | Armeniades ....... | A61B 5/02216 600/561 |

(Continued)

FOREIGN PATENT DOCUMENTS

WO  2012092018 A1  7/2012

*Primary Examiner* — Lauren P Farrar (57) ABSTRACT

Ophthalmic surgical devices, systems, and methods for regulating aspiration from a patient's eye are provided. A vacuum pump in fluid communication with an aspiration line provides fluid aspiration from a vitreous chamber of the eye through the aspiration line. A sensor disposed adjacent to or inside the eye determines sensor data relating to an intraocular pressure (IOP). The controller receives the sensor data and regulates the aspiration in response to changes in the IOP, such as by controlling the vacuum pump. The controller may determine whether a fluid infusion to the vitreous chamber through an infusion line is below a maximum infusion level, regulate the infusion in response to the IOP being below a threshold value and the infusion being below the maximum infusion level, and regulate the aspiration in response to the IOP being below the threshold value and the infusion being at or above the maximum infusion level.

15 Claims, 6 Drawing Sheets

(56) References Cited

U.S. PATENT DOCUMENTS

| | | | |
|---|---|---|---|
| 5,865,764 | A | 2/1999 | Moorhead |
| 7,326,183 | B2 | 2/2008 | Nazarifar et al. |
| 7,470,277 | B2 | 12/2008 | Finlay et al. |
| 7,524,299 | B2 | 4/2009 | Hopkins et al. |
| 7,713,237 | B2 | 5/2010 | Nazarifar et al. |
| 8,246,580 | B2 | 8/2012 | Hopkins et al. |
| 8,430,840 | B2 | 4/2013 | Nazarifar et al. |
| 9,517,162 | B2 | 12/2016 | Huculak et al. |
| 9,931,447 | B2 | 4/2018 | Layser et al. |
| 2010/0280435 | A1* | 11/2010 | Raney ............... A61F 9/00745 604/22 |
| 2012/0215160 | A1* | 8/2012 | Valenti ............... A61F 9/00736 604/31 |
| 2013/0150782 | A1 | 6/2013 | Sorensen et al. |
| 2014/0074011 | A1* | 3/2014 | Charles ............... A61F 9/00745 604/22 |
| 2014/0114236 | A1 | 4/2014 | Gordon |
| 2014/0163455 | A1 | 6/2014 | Wilson et al. |
| 2015/0148836 | A1 | 5/2015 | Heeren |
| 2017/0333253 | A1 | 11/2017 | Heeren et al. |
| 2018/0078415 | A1* | 3/2018 | Citterio ............... A61M 1/0084 |

\* cited by examiner

AUTOMATED ASPIRATION THROTTLING IN VITREORETINAL SURGERY

PRIORITY CLAIM

This application claims the benefit of priority of U.S. Provisional Patent Application Ser. No. 62/333,928 titled "Automated Aspiration Throttling in Vitreoretinal Surgery", filed on May 10, 2016, whose inventors are Tammo Heeren and Andrew David Johnson, which is hereby incorporated by reference in its entirety as though fully and completely set forth herein.

TECHNICAL FIELD

The present disclosure relates to ophthalmic surgical devices, systems, and methods. More particularly, but not by way of limitation, the present disclosure relates to devices, systems, and methods for regulating aspiration from a patient's eye during an ophthalmic surgical procedure.

BACKGROUND

Microsurgical procedures frequently require precision cutting and/or removing of various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

During vitreoretinal surgery, a microsurgical cutting probe of a vitreous cutter is used to cut the vitreous and/or membranes in the vitreous chamber and aspirate away the cut tissue. These cutting probes may include a hollow outer cutting member, a hollow inner cutting member arranged coaxially with and movably disposed within the hollow outer cutting member, and a port extending radially through the outer cutting member near the distal end thereof. Vitreous humor and/or membranes are aspirated into the open port, and the inner member is actuated, closing the port. As the port closes, cutting surfaces on both the inner and outer cutting members cooperate to cut the vitreous and/or membranes, and the cut tissue is then aspirated away through the inner cutting member.

Many complications can arise during vitreoretinal surgery procedures. Some of these complications may arise because of the nature of the procedures. For example, during removal of vitreous humor, the eye may collapse if an intraocular pressure (IOP) in the vitreous chamber is allowed to drop too much. An infusion line may be used to provide fluid from an infusion chamber of a console to the eye while the aspiration line removes cut tissue to maintain a stable IOP. The infusion pressure of the infusion line may be automatically regulated to prevent such a collapse based on predictions of the IOP at the console using pressure measurements in the infusion chamber and flow rate measurements through the infusion line at the console.

However, if an infusion line is not filled with liquid (e.g., when the infusion line is infusing air or the infusion line is compromised by air bubbles) or becomes kinked or otherwise occluded, the predictions of the IOP at the console are no longer valid. A surgeon may continue aspirating fluid from the eye through the aspiration line, resulting in a drop of the IOP. The console is unable to detect the drop of the IOP due to the occlusion and may simply continue applying pressure on the fluid through the infusion line which is not reaching the eye due to the occlusion, and the eye may start to collapse.

Further, complications may arise when the cutting probe or the aspiration line is occluded. For example, a tip of the cutting probe may be occluded by a piece of the vitreous and/or membranes. A surgeon may increase the vacuum applied to the aspiration line to try to break the occlusion. When the occlusion breaks in response to the increased vacuum, there is a sudden outflow through the aspiration line, resulting in a drop of the IOP. Because the predictions of the IOP are based on measurements taken at the console, there is a delay in detection of the drop of the IOP. During that delay, pressure applied to the fluid through the infusion line is not increased to maintain a stable IOP, and the eye may start to collapse.

Additionally, complications may arise during a fluid/air exchange procedure in which liquid in the eye is aspirated and replaced with air. While the infusion line is infusing air, a surgeon may inadvertently switch from aspirating liquid to air through the aspiration line, which results in a sudden drop of IOP. The pressure of the air infused through the infusion line may be increased to maintain the IOP at desired levels, but this may result in a strong air jet penetrating into the eye, which may damage the eye.

Thus, there is a need for improved ophthalmic surgical devices, systems, and methods.

SUMMARY

In one exemplary aspect, the present disclosure is directed to an ophthalmic surgical system that includes a vacuum pump and a controller for regulating fluid aspiration from a patient's eye during an ophthalmic surgical procedure. The vacuum pump may be in fluid communication with an aspiration line and may be configured to provide fluid aspiration from a vitreous chamber of the patient's eye through the aspiration line. The controller may be configured to receive sensor data relating to an intraocular pressure (IOP) of the patient's eye, monitor for changes in the IOP based on the sensor data, and control the vacuum pump to regulate the fluid aspiration in response to the changes in the IOP.

The system may further include one or more sensors disposed adjacent to or in the patient's eye. The one or more sensors may be configured to determine, at a location adjacent to and/or in the patient's eye, the sensor data, and provide the sensor data to the controller. For example, the system may further comprise an infusion line having a distal end configured to enter into the vitreous chamber, and the one or more sensors may be disposed adjacent to and/or at the distal end of the infusion line. The controller may be configured to determine whether a fluid infusion to the vitreous chamber through the infusion line is below a maximum infusion level, increase the fluid infusion in response to the IOP being below a threshold value and the infusion being below the maximum infusion level, and decrease the fluid aspiration in response to the IOP being below the threshold value and the fluid infusion being at or above the maximum infusion level.

In an additional exemplary aspect, the present disclosure is directed to an ophthalmic surgical system that may include an infusion line, an aspiration line, a hand piece, and a console for regulating aspiration from a patient's eye during an ophthalmic surgical procedure. The infusion line may have a proximal end, a distal end, and an infusion passage extending therethrough, and the distal end of the infusion line may be configured to enter into a vitreous chamber of the patient's eye. The aspiration line may have a proximal end, a distal end, and an aspiration passage extending therethrough. The hand piece may be sized and shaped for grasping by a user and coupled to the distal end of the aspiration line. The console may be coupled to the proximal end of the infusion line and the proximal end of the aspiration line, and includes a vacuum pump, an infusion chamber, an infusion pump, and a controller. The vacuum pump may be in fluid communication with the aspiration passage and may be configured to provide fluid aspiration from the vitreous chamber through the aspiration passage. The infusion chamber may be in fluid communication with the infusion passage, and the infusion pump may be configured to provide fluid infusion from the infusion chamber to the vitreous chamber through the infusion passage. The controller may be configured to receive sensor data relating to an IOP of the patient's eye, and regulate the fluid aspiration in response to changes in the IOP.

The system may further include one or more sensors disposed adjacent to and/or in the patient's eye. The one or more sensors may be configured to determine, at a location adjacent to and/or in the patient's eye, the sensor data, and provide the sensor data to the controller. For example, the one or more sensors may be disposed adjacent to and/or at the distal end of the infusion line. The controller may be configured to determine whether a fluid infusion to the vitreous chamber through an infusion line is below a maximum infusion level, increase the fluid infusion in response to the IOP being below a threshold value and the infusion being below the maximum infusion level, and decrease the fluid aspiration in response to the IOP being below the threshold value and the fluid infusion being at or above the maximum infusion level.

In another exemplary aspect, the present disclosure is directed to a method of treating an ophthalmic condition. The method may include receiving sensor data from a sensor adjacent to or in an eye of a patient, monitoring for changes in an IOP of the eye based on the sensor data, determining whether fluid infusion to a vitreous chamber of the eye through an infusion line is below a maximum infusion level, in response to determining the IOP is below a threshold value and the fluid infusion is below the maximum infusion level, increasing the fluid infusion, and in response to determining the IOP is below the threshold value and the fluid infusion is at or above the maximum infusion level, reducing fluid aspiration from the vitreous chamber through an aspiration line.

The regulating of the fluid aspiration may further be in response to an actuation of a foot pedal. The regulating of the fluid aspiration may include controlling a vacuum pump in fluid communication with the aspiration line.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices, systems, and methods disclosed herein and together with the description, serve to explain the principles of the present disclosure.

These figures will be better understood by reference to the following Detailed Description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the disclosure is intended. Any alterations and further modifications to the described devices, instruments, systems, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to devices, systems, and methods for regulating aspiration from a patient's eye based on an intraocular pressure (IOP) determined using measurements at a location adjacent to or in a patient's eye during ophthalmic surgical procedures, such as surgeries in which the surgeon needs to remove vitreous humor or fluids from the patient's eye. Pressure changes and excessively low or high pressures can complicate the performance of such procedures, putting the patient at risk. In some aspects described herein, an infusion line includes sensors such as a pressure sensor and/or a flow rate sensor disposed adjacent to or at a distal end, which enters into a vitreous chamber of the patient's eye. The devices, systems, and methods disclosed herein may enable a surgeon to better monitor important pressures and to react quickly to pressure drops that arise during an ophthalmic surgical procedure. By improving the surgeon's abilities or by enabling the system to respond to pressure conditions during an ophthalmic surgical procedure, outcomes for patients may be improved.

Figure 1:
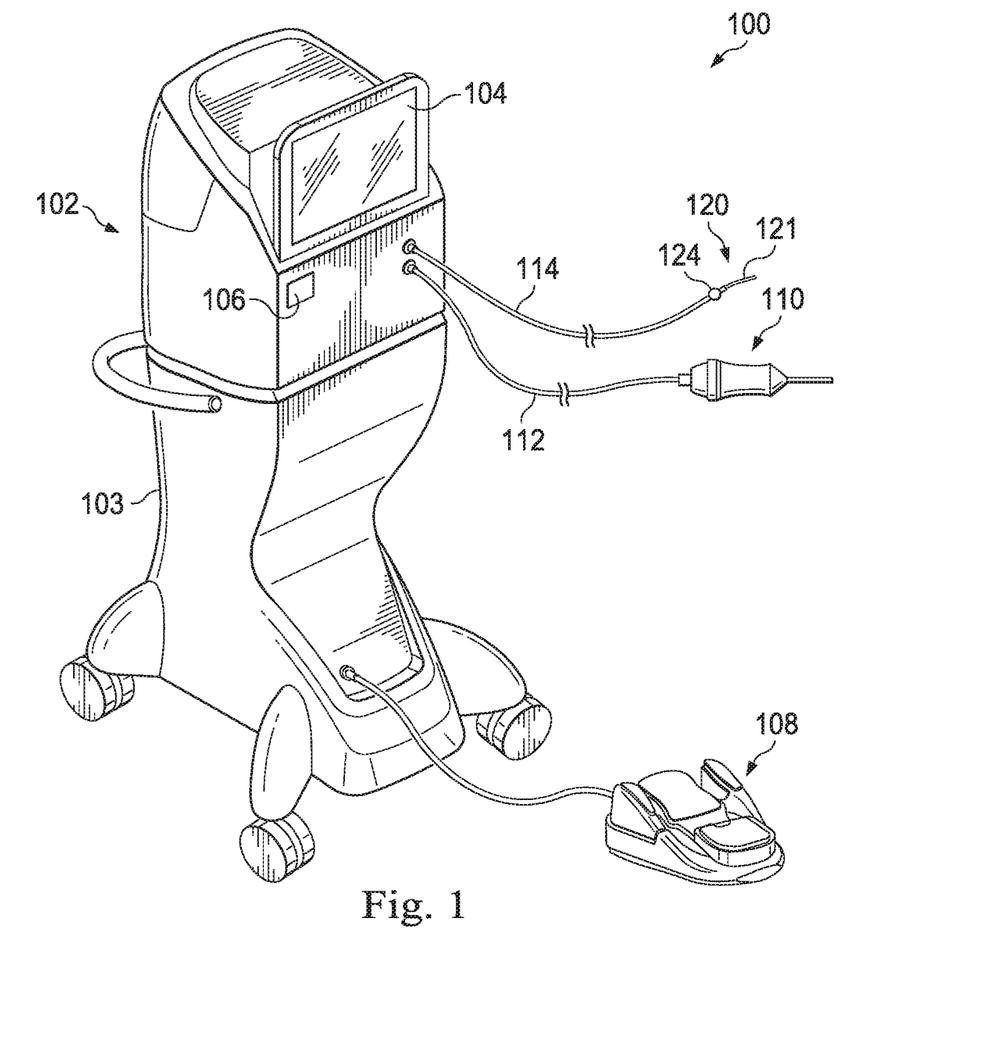
FIG. 1 is an illustration of a surgical system according to exemplary aspects of the present disclosure.
Figure 3:
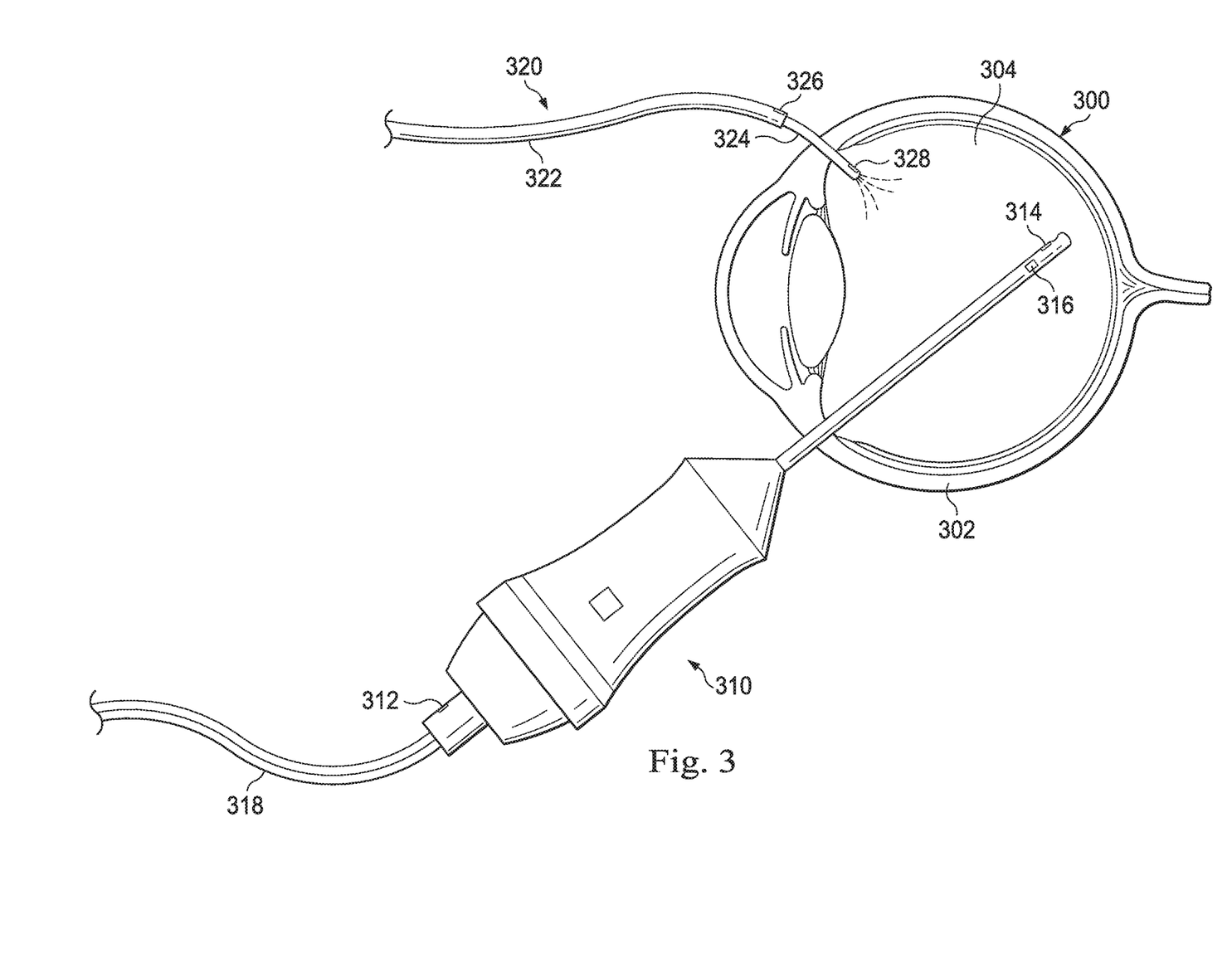
FIG. 3 is an illustration of a hand piece and an infusion line in situ in an eye according to exemplary aspects of the present disclosure.

FIG. 1 illustrates an ophthalmic surgical system 100 according to an exemplary embodiment. The surgical system 100 may include a console 102 that has a mobile base housing 103, an associated display screen 104 that may show data relating to system operations and performance during an ophthalmic surgical procedure, and a foot pedal 108 in communication with the console 102. The surgical system 100 also may include a hand piece 110 that may be utilized during an ophthalmic surgical procedure. Depending on the implementation, the hand piece 110 may be, for example, a vitrectomy cutter hand piece, an ultrasonic hand piece, an aspiration hand piece, or other hand piece. The surgical system 100 may also include an aspiration line 112 having a proximal end coupled to the console 102 and a distal end coupled to the hand piece 110, and an infusion line 114 having a proximal end coupled to the console 102 and a distal end 120 having an infusion tip 121 configured to enter into a vitreous chamber of a patient's eye. The surgical system 100 may also include at least one IOP sensor 124, which may include, for example without limitation, a pressure sensor and/or a flow rate sensor. The IOP sensor 124 may be disposed adjacent to the distal end 120 of the infusion line 114 as shown in FIG. 1. Alternatively, or in addition, the IOP sensor 124 may be disposed at the distal end 120 of the infusion line 114 or at a distal end of the hand piece 110 and configured to enter into the vitreous chamber of the patient's eye, as shown in FIG. 3.

The console 102 of the surgical system 100 includes features that allow for control of the hand piece 110. For example, the aspiration line 112 may include pneumatic and/or electrical supply lines to couple the hand piece 110 to the console 102. The aspiration line 112 may facilitate control and monitoring of the hand piece 110 by transmitting data between the hand piece 110 and the console 102.

The console 102 of the surgical system 100 further includes features that allow communication of sensor data between the IOP sensor 124 and the console 102. For example, the infusion line 114 may include electrical supply lines to couple the IOP sensor 124 to the console 102. The infusion line 114 may facilitate taking measurements at the IOP sensor 124 by transmitting data between the IOP sensor 124 and the console 102.

The console 102 further includes a computer system (FIG. 2) that may include one or more processors in communication with a memory having computer instructions to control the hand piece 110, display information on the display screen 104, and receive and process input commands and data. The surgical system 100 may include a network interface for communication with a network. These features facilitate control and monitoring of the hand piece 110 during operation. Additionally, these features may facilitate the monitoring, data processing, and control for the IOP sensor 124. Some embodiments of the surgical system 100 further include a pressure sensor 106 disposed on or about the housing 103 to sense an ambient pressure. This ambient pressure may be atmospheric pressure.

Some aspects of the surgical system 100, such as the hand piece 110, the infusion line 114, and the IOP sensor 124, are described in further detail in U.S. patent application Ser. No. 14/090,360, filed on Nov. 26, 2013, entitled "Pressure-Sensing Vitrectomy Surgical Systems and Methods," which is hereby incorporated by reference in its entirety.

Figure 2:
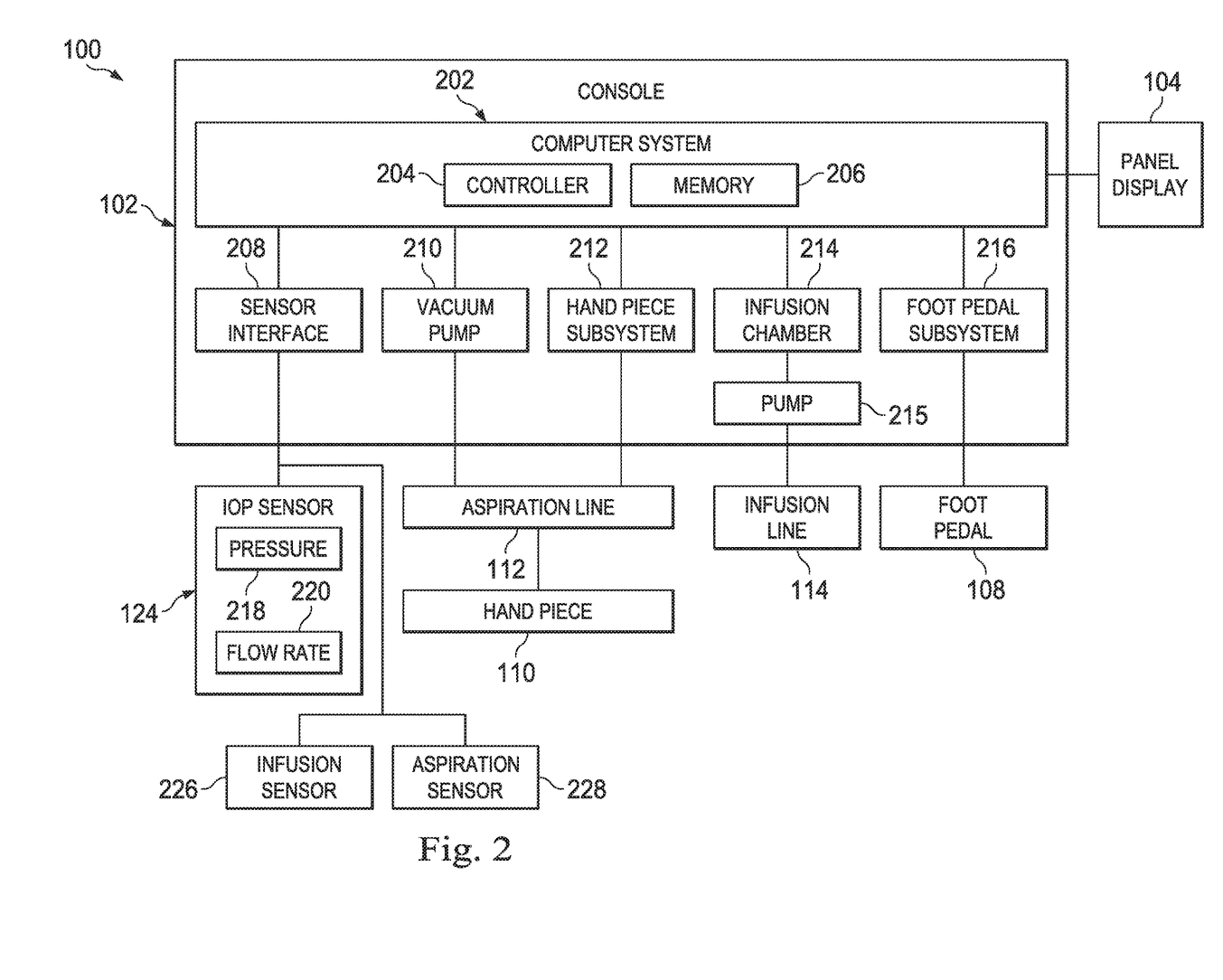
FIG. 2 is a block diagram of the surgical system of FIG. 1 showing various subsystems according to exemplary aspects of the present disclosure.

FIG. 2 is a block diagram of the surgical system 100 of FIG. 1 showing various subsystems. The console 102 includes a computer system 202, which includes a controller 204 and a memory 206. The console 102 further includes a sensor interface 208, a vacuum pump 210 (e.g., a venturi-based pump such as an aspirator or another type of vacuum pump), a hand piece subsystem 212, an infusion chamber 214, an infusion drive mechanism such as an infusion pump 215, and a foot pedal subsystem 216. The infusion pump 215 may be a part of the infusion chamber 214 or may be provide as a separate component coupled to the infusion chamber 214.

The controller 204 may be one or more processors such as microprocessors, logic devices, microcontrollers, application specific integrated circuits (ASICs), programmable logic devices (PLDs), or other suitable processing systems and be configured to run operating systems and applications. The controller 204 is configured to execute computer instructions stored on the memory 206 and access data stored in memory 206. Further, the controller 204 is configured to display information on the panel display screen 104.

The controller 204 is configured to receive, through the sensor interface 208, sensor data relating to an IOP of a patient's eye from the IOP sensor 124, an infusion sensor 226, and/or an aspiration sensor 228. The IOP sensor 124 may be disposed adjacent to the patient's eye during the ophthalmic surgical procedure. The IOP sensor 124 may be configured to determine, at a location adjacent to the patient's eye, the sensor data (e.g., pressure data, flow rate data, or both), and provide the sensor data to the controller 204. For example, in some implementations, the IOP sensor 124 may be disposed adjacent to the distal end 120 of the infusion line 114 such that the IOP sensor 124 is just outside the eye and just upstream of the infusion line 114 during the ophthalmic surgical procedure. The IOP sensor 124 may include a pressure sensor 218 (e.g., fiber optic pressure sensors, electrical pressure sensors such as piezoelectric pressure sensors, microelectromechanical system (MEMS) pressure sensors, or other pressure sensors) that measures a pressure (e.g., a pressure drop just outside the eye, which may not be able to be accurately measured by a pressure sensor located inside the console 102) and/or a flow rate sensor 220 that measures a flow rate of fluid through a tubing such as the infusion line 114. The controller 204 may calculate an IOP value, such as a predicted IOP value, based on the sensor data, which may include one or both of the pressure data and the flow rate data.

Alternatively, or in addition, the IOP sensor 124 may be disposed inside the patient's eye during the ophthalmic surgical procedure. The IOP sensor 124 may be configured to determine, at a location in the vitreous chamber, the sensor data, and provide the sensor data to the controller 204. For example, the IOP sensor 124 may be disposed at the distal end 120 of the infusion line 114 such that the IOP sensor 124 is in the vitreous chamber of the patient's eye during the ophthalmic surgical procedure. The IOP sensor 124 may include the pressure sensor 218 that measures pressure. The controller 204 may calculate an IOP value, which may be an actual IOP value given that the IOP sensor 124 is located in the patient's eye, based on the sensor data, which includes the pressure data.

Implementations including the infusion sensor 226 or the aspiration sensor 228 monitor or detect the flow rate of fluid entering the patient's eye or leaving the patient's eye. For example, the infusion sensor 226 may be associated with the infusion line 114 in a manner permitting it to monitor or detect pressure in the line, flow through the line, or some other parameter indicative of pressure or flow. In some implementations, the infusion sensor 226 monitors a pump speed of the infusion pump 215. In some such implementations, the infusion sensor is simply feedback from a processor or motor on the pump 215 indicative of the pump speed. In some implementations, the infusion sensor 226 may include a pressure sensor or flow rate sensor as described above with reference to the IOP sensor.

In a similar manner, the aspiration sensor 228 may be associated with the aspiration line 112 or hand piece 110 in a manner permitting it to monitor or detect pressure in the line, flow through the line, or some other parameter indicative of pressure or flow. In some implementations, the aspiration sensor 228 monitors a pump speed of the vacuum pump 210. In some such implementations, the aspiration sensor 228 is simply feedback from a processor or motor on the vacuum pump 210 indicative of the pump speed. In some implementations, the aspiration sensor 228 may include a pressure sensor or flow rate sensor as described above with reference to the IOP sensor.

The aspiration line 112 may be used to remove fluid (e.g., a liquid, a gas, a viscoelastic material, a mixture of liquids and solids, a mixture of liquids and gases, or other fluid), which may include cut vitreous and/or membranes, out of the vitreous chamber. The vacuum pump 210 is in fluid communication with the aspiration line 112. The aspiration line 112 has the proximal end coupled to the console 102, the distal end coupled to the hand piece 110, and an aspiration passage extending therethrough. In some implementations, the hand piece 110 may include a port at its proximal end fluidically coupled to the aspiration line and a tip at the distal end configured to enter into the vitreous chamber of the patient's eye, and an aspiration passage extending therethrough. The vacuum pump 210 is in fluid communication with the aspiration passage through the aspiration line 112 and the hand piece 110, and the aspiration passage is in fluid communication with the vitreous chamber of the patient's eye. The vacuum pump 210 is configured to provide fluid aspiration from the vitreous chamber through the aspiration passage of the aspiration line 112 and the hand piece 110.

The hand piece 110 may be in communication with the hand piece subsystem 212 via a pneumatic or electrical line provided in the aspiration line 112. The controller 204, which is in communication with the hand piece subsystem 212, may control one or more aspects of the hand piece 110, such as an on or off state or a cutting rate of the hand piece 110.

The infusion line 114 is used to deliver fluid (e.g., a liquid such as balanced salt solution (BSS), a gas such as air, or other fluid) such as replacement fluid or irrigation fluid from the infusion chamber 214 into the vitreous chamber. The infusion chamber 214 is in fluid communication with the infusion line 114. The infusion line 114 may have the proximal end coupled to the console 102, the distal end (e.g., an engagement member) 120 configured to enter into the vitreous chamber of the patient's eye, and an infusion passage extending therethrough. The infusion chamber 214 may be in fluid communication with the infusion passage through the infusion line 114, and the infusion passage is in fluid communication with the vitreous chamber of the patient's eye. The infusion chamber 214 includes fluid and is configured to provide fluid infusion into the vitreous chamber through the infusion passage of the infusion line 114. Some implementations employ the infusion pump 215 to infuse fluid to or otherwise irrigate the surgical site. The infusion pump 215 may be any of a variety of types of pumps, including a peristaltic pump, a syringe pump, a pressurized fluid pump, or some other infusion pump. Control of the pump may permit the computer system 202 to increase, decrease, or hold steady flow through the pump based on received information from the infusion sensor 226, the foot pedal subsystem, or other information. In some implementations, the computer system 202 may include a pre-stored threshold that serves as an upper limit for fluid flow rate or pressure introduced to the surgical site through the infusion line. In such implementations, if the requested fluid amount exceeds the threshold, the infusion pump 215 may be disabled or its speed may be capped to avoid damage to the sensitive tissues in the patient's eye.

The foot pedal 108 receives actuation from a foot of a user and transmits actuation data to the foot pedal subsystem 216. The foot pedal subsystem 216 includes an interface between the foot pedal 108 and the controller 204, and may receive actuation data from the foot pedal 108, process the actuation data, and transmit the actuation data to the controller 204. The controller 204 receives the actuation data from the foot pedal subsystem 216 and, in response, may regulate fluid aspiration through the aspiration line 112, fluid infusion through the infusion line 114, and/or one or more aspects of the hand piece 110 based on the actuation data, as further described herein. The foot pedal 108 may be a wired foot pedal as shown in FIG. 1 or a wireless foot pedal.

The controller 204 monitors for changes in the IOP based on the sensor data, and regulates the fluid aspiration from the vitreous chamber of the patient's eye through the aspiration line 112 based on the changes in the IOP. In some implementations, the controller 204 may control the vacuum pump 210 to regulate the fluid aspiration from the vitreous chamber. For example, the controller 204 may control the vacuum pump 210 by reducing a negative pressure (e.g., a pressure relative to the atmospheric pressure) generated by the vacuum pump 210 in response to the IOP (e.g., an IOP value such as a predicted IOP value or an actual IOP value) falling below a threshold IOP level (e.g., a threshold value). Pressures referred to herein may be gauge pressures rather than absolute pressures. In another example, the controller 204 may control the vacuum pump 210 by turning off the vacuum pump 210, and may subsequently turn on the vacuum pump 210 in response to the IOP rising above the threshold and/or an actuation of the foot pedal 108. Accordingly, the controller 204 may perform automatic braking of the fluid aspiration through the aspiration line 112. In a further example, the controller 204 may control the vacuum pump 210 by determining a difference between the IOP and a target IOP level (e.g., a target value or range) and adjusting the vacuum pump to reduce the difference between the IOP and the target IOP level.

Alternatively, or in addition, the controller 204 may control a vacuum limiter associated with the aspiration line 112 to regulate the fluid aspiration through the aspiration line 112. The vacuum limiter reduces the negative pressure generated by the vacuum pump 210 at a location other than the vacuum pump 210. For example, the vacuum limiter may include an opening formed in a wall of the aspiration passage, an actuator disposed in the opening, and a biasing element biasing the actuator to a closed position that prevents passage of fluid through the opening. The biasing element may have a structure to permit the actuator to displace from a closed position to a relief position such that fluid may pass through the opening. The controller 204 may control the vacuum limiter by displacing the actuator to the relief position to regulate the fluid aspiration. The vacuum limiter may be provided on the hand piece 110. Alternatively, the vacuum limiter may be provided on the aspiration line 112 at a location in or outside the console 102.

FIG. 3 illustrates a cross-sectional view of an eye 300 undergoing a procedure involving a hand piece 310 (e.g., the hand piece 110 in FIGS. 1 and 2) and an infusion line or infusion cannula 320 (e.g., the infusion line 114 in FIGS. 1 and 2). Both the hand piece 310 and the infusion line 320 may be coupled to a console (e.g., the console 102 in FIGS. 1 and 2). In FIG. 3, the hand piece 310 and the infusion line 320 are respectively inserted through the sclera 302 and into the vitreous chamber 304 of the eye 300. The infusion line 320 is used to deliver fluid such as replacement fluid or irrigation fluid into the vitreous chamber 304 during an ophthalmic surgical procedure (e.g., vitrectomy, fluid/air exchange, air/gas exchange, silicone oil injection, and/or other ophthalmic surgical procedures). Fluid infusion may be regulated by increasing or decreasing a pressure level of the irrigation fluid by a surgical system (e.g., the surgical system 100 of FIGS. 1 and 2). The hand piece 310 may be a vitrectomy cutter hand piece, an ultrasonic hand piece, or other aspiration hand piece.

The infusion line 320 includes a flexible elongate member 322. Some implementations include a rigid engagement member 324 (e.g., the distal end 120 in FIG. 1) affixed at the distal end. The rigid engagement member 324 may be more ridged than the flexible elongate member 322. The flexible elongate member 322 and the rigid engagement member 324 have a central lumen (e.g., an infusion passage) running therethrough. The infusion line 320 may provide fluid to the vitreous chamber 304 from a fluid source (e.g., the infusion chamber 214 in FIGS. 1 and 2), carried through the central lumen, in order to maintain an appropriate IOP as portions of the vitreous humor and/or fluid in the vitreous chamber 304 are removed.

In some implementations, the infusion line 320 may include one or more pressure sensors, for example, a pressure sensor 326, a pressure sensor 328, or both. In some implementations, one or more of the pressure sensors 326 and 328 may correspond with the IOP sensor 124, and in some implementations, one or more of the pressure sensors 326 and 328 may correspond with the infusion sensor 226. The pressure sensor 326 may be disposed on the infusion line 320 and adjacent to the distal end of the infusion line 320 such that it remains outside, but in close proximity to, the eye 300 during the ophthalmic surgical procedure. In some implementations, the pressure sensor 328 may sense a pressure just outside the eye 300, which may be used to determine the IOP (e.g., an actual IOP value or a predicted IOP value that is closer to an actual IOP value than possible using sensors located in the console) during the surgical procedure. In some implementations, the pressure sensor 328 is disposed on the rigid engagement member 324 (e.g., at a distal portion of the rigid engagement member 324) such that it enters into the vitreous chamber 304 during the ophthalmic surgical procedure. The pressure sensor 328 may sense an internal eye pressure in the vitreous chamber 304, which may be used to determine the IOP (e.g., an actual IOP value) during the surgical procedure.

Depending on the implementation, the hand piece 310 may include one or more pressure sensors, such as a pressure sensor 312, a pressure sensor 314, and/or a pressure sensor 316. Each of the pressure sensors 312, 314, and 316 may measure a pressure at a different location. In some implementations, one or more of the pressure sensors 312, 314, and 316 may correspond with the IOP sensor 124, and in some implementations, one or more of the pressure sensors 326 and 328 may correspond with the aspiration sensor 228. Depending on the implementation, the pressure sensor 312 may be disposed on a housing of the hand piece 310 and may measure an ambient pressure such as atmospheric pressure. In some examples, the ambient pressure sensor 312 is provided as pressure sensor 106 on an exterior surface of the console 102, as shown in FIG. 1. The pressure sensors 314 and 316 may be disposed at a tip (e.g., a cutter) of the hand piece 310. The pressure sensor 314 may be disposed on the hand piece 310 and may measure an internal eye pressure in the vitreous chamber 304 outside the cutter, which may be used to determine the IOP (e.g., an actual IOP value) during the ophthalmic surgical procedure. The pressure sensor 316 may be disposed within the tip so as to measure an internal pressure that is internal to the hand piece, which may be used to characterize the vacuum supplied through an aspiration line 318 (e.g., the aspiration line 112 in FIGS. 1 and 2) to the hand piece 310.

In addition to their respectively sensed pressures, pressure sensors 312, 314, 316 326, and/or 328 may be used in conjunction to provide a differential pressure, such as a pressure representative of the IOP of the eye 300. Generally, the IOP is a gauge pressure reading determined by the difference between the absolute pressure in the eye (as measured by a pressure sensor in the eye such as the pressure sensor 314 and/or 328) and atmospheric pressure (as measured by the pressure sensor 312 and/or pressure sensor 106 in FIG. 1). Therefore, in some exemplary embodiments, pressure readings of pressure sensor 314 and/or 328 are taken simultaneously or nearly simultaneously with pressure readings of ambient pressure sensor 312 and/or 106 so that the actual IOP can be calculated as a function of the measured pressures.

The pressure sensors 312, 314, 316, 326, and 328 may each be a fiber optic pressure sensor, an electrical pressure sensor such as a piezoelectric pressure sensor, a MEMS (Micro-Electro-Mechanical Systems) pressure sensor, or another pressure sensor. The pressure sensors 314, 316, and 328 may be miniaturized pressure sensors capable of entering a small orifice through which the cutter of the hand piece 310 or the engagement member 324 enters the eye 300. As the pressure sensors 312 and 326 are disposed outside the eye and do not enter the eye through the small orifice, the pressure sensors 312 and 326 do not have size constraints and, thus, are not limited to such miniaturized pressure sensors. Accordingly, the pressure sensors 312 and 326 may be any appropriate type of pressure sensor.

The pressures that may be sensed by the hand piece 310 and/or the infusion line 320 facilitate improved control by the surgical system by providing additional information that can be processed by the surgical system and used for automated flow and pressure control. For example, by measuring and determining the IOP of the eye 300, the surgical system may be able to avoid the collapse of the eye 300 due to excessive removal of vitreous humor and/or fluid from the vitreous chamber 304 or the inadequate replacement of the vitreous humor with fluid (e.g., balanced salt solution, air, or other appropriate replacement fluid) through the infusion line 320 during an ophthalmic surgical procedure by increasing fluid infusion such as by increasing a pressure level of the replacement fluid, decreasing fluid aspiration by decreasing the vacuum or negative pressure generated by a vacuum pump (e.g., the vacuum pump 210 in FIG. 2), decreasing the cutting rate of hand piece 310, otherwise adjusting these parameters or other parameters, or a combination thereof. Further, the internal pressure or differential pressure may provide the surgical system with data regarding the performance of the hand piece 310 in removing vitreous humor.

As illustrated in FIG. 3, some embodiments may include redundant pressure sensors. For example, the pressure sensor 328 of the infusion line of 320 may be considered redundant due to the presence of the pressure sensor 314 of the hand piece 310. In some embodiments, only one pressure sensor to measure an internal eye pressure may be provided by the combined use of the hand piece 310 and the infusion line 320, such that either the hand piece 310 or the infusion line 320 includes a pressure sensor within the vitreous chamber 304. Similarly, in some embodiments only one ambient pressure sensor is present. In other embodiments, data for a single pressure is obtained using multiple pressure sensors. The data from each pressure sensor may be provided directly or a mathematical combination of the pressure sensors may be used to provide a single value. Using the pressure measurements obtained from the pressure sensors depicted in FIG. 3, the surgical system may automatically control fluid aspiration and/or fluid infusion and, further, may allow a surgeon to exercise improved control of hand piece 310 and the infusion line 320 during a surgical procedure.

Figure 4:
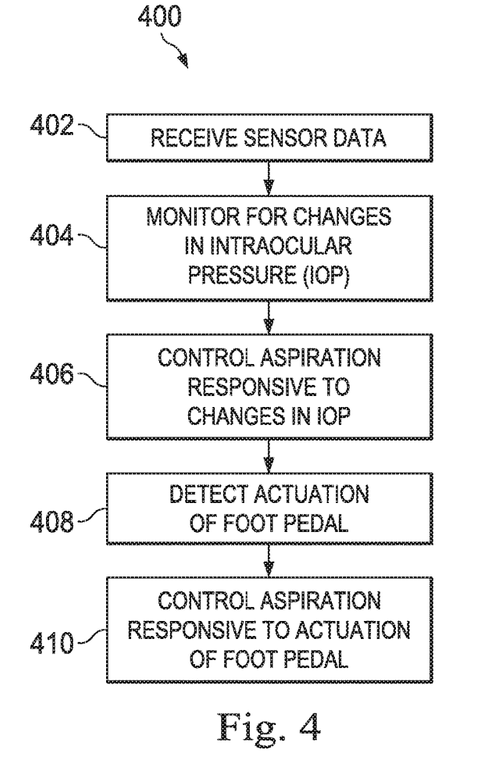
FIG. 4 is a flowchart showing a process performed by the surgical system of FIGS. 1 and 2 for regulating aspiration responsive to changes in intraocular pressure (IOP) during an ophthalmic surgical procedure according to exemplary aspects of the present disclosure.

FIG. 4 is a flowchart showing a process 400 performed by the surgical system 100 of FIGS. 1 and 2 for regulating fluid aspiration from a patient's eye during an ophthalmic surgical procedure.

At block 402, a controller such as the controller 204 of the surgical system 100 receives sensor data from one or more sensors such as the IOP sensor 124 disposed adjacent to or in the patient's eye.

At block 404, the controller 204 monitors for changes in IOP. The controller 204 may determine an IOP (e.g., an IOP value such as a predicted IOP value or an actual IOP value) based on the sensor data and detect changes in the IOP.

At block 406, the controller 204 regulates fluid aspiration responsive to the changes in the IOP. The controller 204 may control a vacuum pump such as the vacuum pump 210 to regulate the fluid aspiration in response to the changes in the IOP. The vacuum pump 210 is in fluid communication with an aspiration line such as the aspiration line 112 and provides fluid aspiration from a vitreous chamber of the patient's eye through the aspiration line 112.

For example, the controller 204 may provide threshold control of the vacuum pump 210 such that in response to the IOP falling below a threshold such as a threshold IOP level (e.g., a threshold value), the controller 204 automatically reduces a negative pressure generated by the vacuum pump 210. Further, the controller 204 may, in response to the IOP rising above the threshold, automatically increase the negative pressure. In another example, the controller 204 may provide on/off control of the vacuum pump 210 such that in response to the IOP falling below a threshold, the controller 204 automatically turns off the vacuum pump 210. Further, the controller 204 may, in response to the IOP rising above the threshold, automatically turn on the vacuum pump 210. In a further example, the controller 204 may provide control-loop feedback control such as proportional-integral-derivative (PID) control of the vacuum pump 210. The controller 204 may determine a difference between the IOP and a target IOP level (e.g., a target value or range) and, in response, automatically adjust the vacuum pump 210 to reduce the difference between the IOP and the target IOP level. Advantageously, the surgical system 100 safeguards against low IOP and prevents collapsing of the eye.

In some implementations, the regulation of the fluid aspiration, by control of the vacuum pump 210 or otherwise, may be coordinated with regulation of the fluid infusion. The controller 204 may prioritize regulating fluid infusion, prioritize regulating fluid aspiration, or simultaneously regulate fluid infusion and fluid aspiration.

Figure 5:
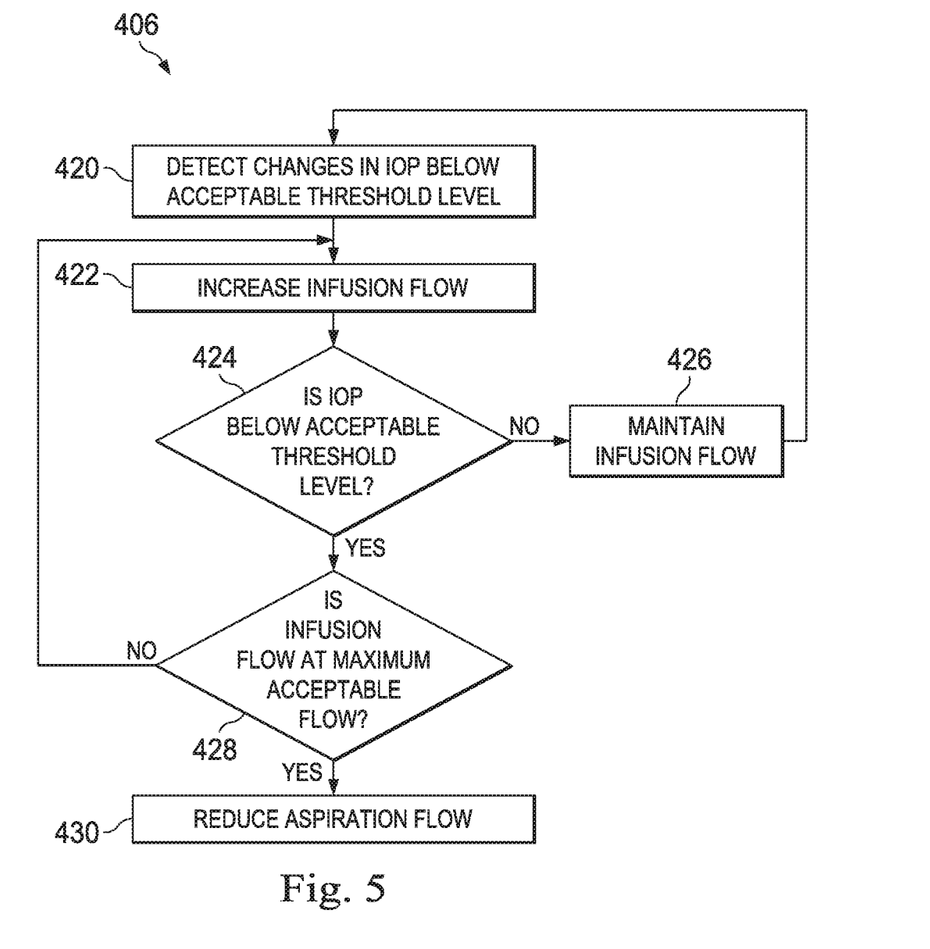
FIG. 5 is a flowchart showing a process performed by the surgical system of FIGS. 1 and 2 for infusion-prioritized regulation responsive to changes in IOP during an ophthalmic surgical procedure according to exemplary aspects of the present disclosure.
Figure 6:
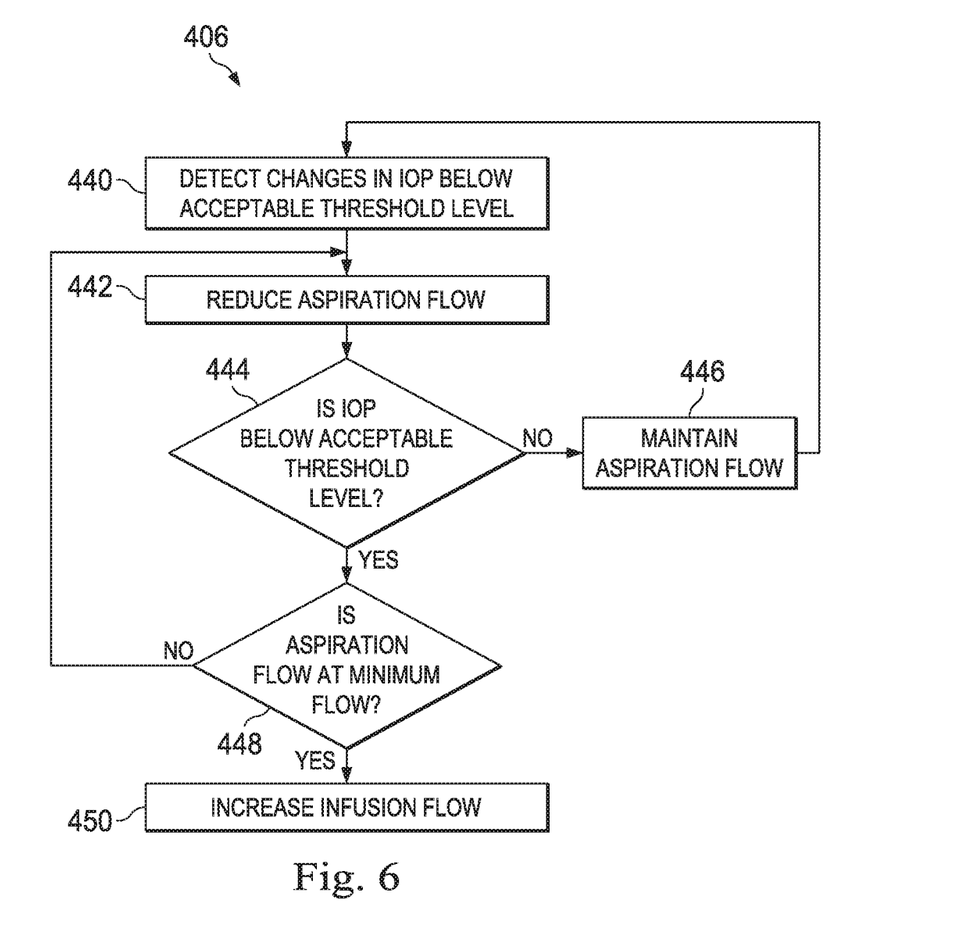
FIG. 6 is a flowchart showing a process performed by the surgical system of FIGS. 1 and 2 for aspiration-prioritized regulation responsive to changes in IOP during an ophthalmic surgical procedure responsive to changes in IOP according to exemplary aspects of the present disclosure.

FIGS. 5 and 6 show exemplary implementations of prioritized irrigation and aspiration control in order to regulate aspiration responsive to changes in IOP. Accordingly, FIGS. 5 and 6 each show different implementations that may make up a part of block 406 in FIG. 4. FIG. 5 shows an implementation prioritizing infusion, and FIG. 6 shows an implementation prioritizing aspiration.

As will be described with reference to FIG. 5, if the controller 204 prioritizes regulating infusion, the controller 204 will only regulate aspiration when infusion has already been increased to a preset maximum infusion level.

Accordingly, turning to FIG. 5, at block 420, the controller 204 may detect changes in IOP that are outside an acceptable IOP range. In some examples, the changes in IOP may be realized by comparing the IOP, as directly measured or calculated based on data from the sensors, to stored ranges or thresholds indicating an acceptable IOP for a particular patient or a particular procedure.

When the IOP is below a threshold and the infusion is below the maximum infusion level, the controller 204 increases the infusion flow (e.g., by increasing the infusion pressure applied at the infusion chamber 214) at block 422. This may be done by controlling the pump 215 to increase the pump speed or taking other action to increase the flow of infusion fluid. At block 424, the controller 204 may monitor information from the sensors to determine whether the IOP is below the threshold IOP level. If the condition at block 424 is no, then at block 426 the controller 204 may maintain the infusion flow. If the condition at block 424 is yes, then at block 428 the controller 204 may determine whether the infusion is already at the prestored maximum acceptable infusion flow level. If the condition at block 428 is no, then the controller 204 may continue to increase the infusion flow at block 422. If the condition at block 428 is yes, then at block 430 the controller 204 reduces or turns off the aspiration (e.g., by reducing the negative pressure generated by, or turning off, the vacuum pump 210).

As will be described with reference to FIG. 6, if the controller 204 prioritizes regulating aspiration, the controller 204 will only regulate infusion when aspiration has already been reduced to a preset minimum aspiration level or turned off.

Accordingly, turning to FIG. 6, at block 440, the controller 204 may detect changes in IOP that are outside an acceptable IOP range. In some examples, the changes in IOP may be realized by comparing the IOP, as directly measured or calculated based on data from the sensors, to stored ranges or thresholds indicating an acceptable IOP for a particular patient or a particular procedure.

When the IOP is below a threshold and the aspiration is above the minimum aspiration level, the controller 204 reduces or turns off the aspiration flow (e.g., by reducing the negative pressure applied by, or turning off, the vacuum pump 210) at block 442. This may be done by controlling the vacuum pump 210 to reduce the pump speed or taking other action to reduce the flow of aspiration fluid. At block 444, the controller 204 may monitor information from the sensors to determine whether the IOP is below the threshold IOP level. If the condition at block 444 is no, then at block 446 the controller 204 may maintain the aspiration flow. If the condition at block 444 is yes, then at block 448 the controller 204 may determine whether the aspiration is still turned on or has not yet been reduced below the prestored minimum acceptable aspiration flow level. If the condition at block 448 is no, then the controller 204 may continue to reduce the aspiration flow at block 442. If the condition at block 448 is yes, then at block 450 the controller 204 increases infusion flow (e.g., by controlling the pump 215 to increase the pump speed or taking other action to increase the flow of infusion fluid).

In a further example, the controller 204 simultaneously regulates infusion and aspiration. In response to the IOP being below a threshold IOP level, the controller 204 simultaneously regulates infusion and aspiration by adjusting both the infusion (e.g., by controlling pressure at the infusion chamber 214) and the aspiration (e.g., by controlling the negative pressure at the vacuum pump 210) in a coordinated fashion.

Alternatively, the regulation of fluid infusion and the regulation of fluid aspiration are separately controlled, each having its own parameters, thresholds, and/or control operations or mechanisms. One skilled in the art will recognize that other control operations or mechanisms may be utilized to regulate/control the fluid aspiration through the aspiration line 112, the fluid infusion through the infusion line 114, the vacuum pump 210, and/or the infusion chamber 214.

At block 408, the controller 204 detects an actuation of a foot pedal such as the foot pedal 108 by a user. The controller 204 may detect the actuation of the foot pedal 108 through a foot pedal subsystem such as the foot pedal subsystem 216. The controller 204 may receive actuation data from the foot pedal 108 through the foot pedal subsystem 216. The actuation data may indicate, for example, whether the foot pedal 108 is actuated, how far the foot pedal 108 is depressed, and/or how fast the foot pedal 108 is depressed.

At block 410, the controller 204 regulates the fluid aspiration responsive to actuation of the foot pedal 108. The controller 204 may further control the vacuum pump 210 to regulate the fluid aspiration from the vitreous chamber of the patient's eye through the aspiration line 112. For example, if the controller 204 provides on/off control, the controller 204 may, in response to the actuation of the foot pedal 108, turn on the vacuum pump 210. In another example, if the controller 204 provides control-loop feedback control, the controller 204 may, in response to the actuation of the foot pedal 108, adjust the vacuum pump 210 such as by adjusting the vacuum or negative pressure generated by the vacuum pump 210 (e.g., increasing or decreasing the negative pressure), or by adjusting the target IOP level (e.g., increasing or decreasing the target IOP level).

Figure 7:
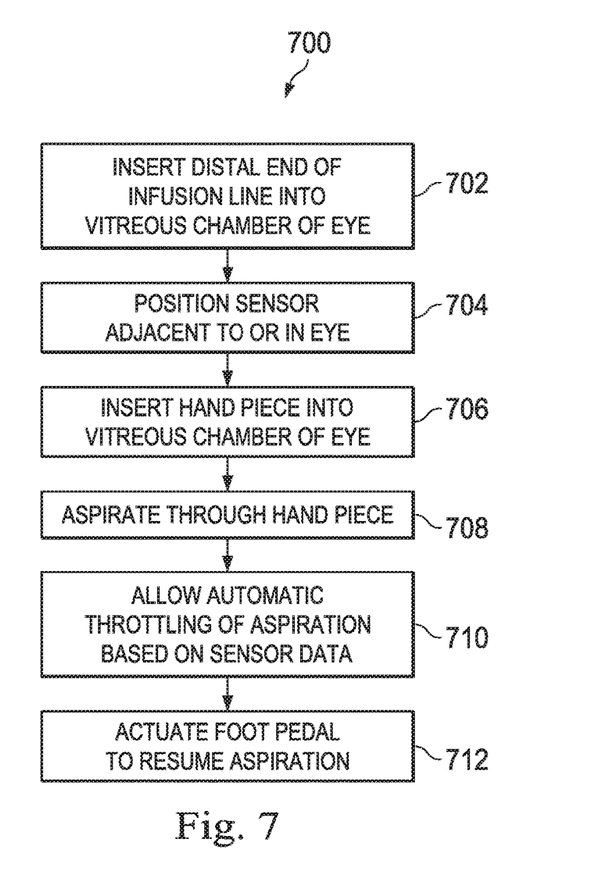
FIG. 7 is a flowchart showing a process for operating the surgical system of FIGS. 1 and 2 during an ophthalmic surgical procedure according to exemplary aspects of the present disclosure.

FIG. 7 is a flowchart showing a process 700 for operating the surgical system 100 of FIG. 1 during an ophthalmic surgical procedure.

At block 702, a user, such as a surgeon performing the ophthalmic surgical procedure, may insert a distal end of an infusion line such as the distal end (e.g., the engagement member) 120 of the infusion line 114 into a vitreous chamber of the patient's eye.

At block 704, the user inserts a tip of a hand piece such as the hand piece 110 into the vitreous chamber of the patient's eye. The hand piece 110 is coupled to a distal end of an aspiration line such as the aspiration line 112.

At block 706, the user may position a sensor such as the IOP sensor 124 adjacent to (e.g., in close proximity to) or inside a patient's eye. In embodiments in which the IOP sensor 124 is disposed adjacent to and/or at the distal end 120 of the infusion line 114 (e.g., pressure sensor 326 and/or 328 in FIG. 3), block 706 is accomplished by performing block 702. In embodiments in which the IOP sensor 124 is disposed on the tip of the hand piece 110 (e.g., pressure sensor 314 in FIG. 3), block 706 is accomplished by performing block 704. In other embodiments, the IOP sensor 124 is coupled to a separate line from the aspiration line 112 and the infusion line 114, and the user places the IOP sensor 124 adjacent to and/or in the patient's eye separately from the aspiration line 112 and the infusion line 114.

At block 708, the user aspirates fluid from the vitreous chamber of the patient's eye through the hand piece 110 and the aspiration line 112, which is in fluid communication with a vacuum pump in the console such as the vacuum pump 210 in the console 102. The user may actuate and/or control aspiration via a foot pedal such as the foot pedal 108.

At block 710, the user allows automatic throttling of the aspiration based on sensor data measured by the IOP sensor 124. The surgical system 100 (e.g., by the controller 204) automatically regulates the fluid aspiration based on the sensor data measured by the IOP sensor 124, as further described above in connection with controller 204 of FIG. 2 and block 406 of FIG. 4. For example, the surgical system 100 may automatically turn off the vacuum pump 210 or reduce a negative pressure generated by the vacuum pump in response to the IOP being larger than (or equal to or larger than) a threshold IOP level (e.g., a threshold value).

At block 712, the user actuates the foot pedal 108 to control the fluid aspiration. For example, the user may re-engage the foot pedal 108 to turn on the vacuum pump 210 to resume fluid aspiration from the vitreous chamber of the patient's eye or increase the negative pressure generated by the vacuum pump.

In an illustrative but non-limiting example, the surgical system 100 of FIGS. 1 and 2 discussed above may be advantageously utilized during a fluid/air exchange procedure. During the fluid/air exchange, the surgeon's objective is to drain the eye of liquid such as BSS and replace the liquid with air. Often during the process, the surgeon may inadvertently switch between liquid aspiration and air aspiration in order to ensure all the liquid is removed. Due to the large difference in fluid viscosity between the liquid and the air, switching between phases will cause a large change in pressure in the eye. A surgical system may use a sensor located in the console to detect the change in pressure, and adjust the infusion setting to compensate until the pressure reading at the console (e.g., the predicted IOP) is at a set point. However, the pressure reading at the console often does not equal the pressure in the eye (e.g., the actual IOP), and there is a delay in detection of the change in pressure at the console because the console is connected to the eye through a long tubing of the infusion line. A surgical system may use a sensor located in or near the eye and adjust infusion to a higher level to compensate for the pressure change, but this may lead to excessive and potentially damaging air jets in the eye.

Advantageously, the surgical system 100 may resolve one or more of these problems. The surgical system 100 may use the IOP sensor 124 located in or near the eye to determine a pressure change such as a change in IOP. When the IOP reaches or falls below a threshold IOP level, the surgical system may increase infusion (e.g., by increasing a pressure applied by the infusion chamber 214) to provide compensation. If the infusion reaches or is at a predetermined limit (e.g., a maximum infusion level), the surgical system 100 provides the difference in compensation by automated throttling down of the aspiration (e.g., by reducing a negative pressure generated by, or turning off, the vacuum pump 210). As the surgeon moves the aspiration tip of the hand piece 110 back into the liquid from the air, the required infusion level would drop and the surgical system 100 throttles aspiration back up accordingly.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic surgical system, comprising:
    a vacuum pump in fluid communication with an aspiration line, the vacuum pump being configured to provide fluid aspiration from a vitreous chamber of an eye of a patient through the aspiration line; and
    an infusion line having a distal end configured to enter into the vitreous chamber and carry an infusion fluid to the vitreous chamber;
    an infusion pump configured to provide the infusion fluid to the vitreous chamber through the infusion line; and
    a controller configured to:
        receive sensor data relating to an intraocular pressure (IOP) of the eye, the sensor data being determined at a location adjacent to or in the eye;
        monitor for changes in the IOP based on the sensor data;
        determine whether fluid infusion to the vitreous chamber of the eye through the infusion line is below a maximum infusion level;
        in response to determining the IOP is below a threshold value and the fluid infusion is at or above the maximum infusion level, control the vacuum pump to reduce the fluid aspiration from the vitreous chamber through the aspiration line based on the changes in the IOP, wherein the controller comprises a proportional-integral-derivative (PID) control used to determine a difference between the IOP and the threshold value and automatically adjust the vacuum pump to reduce the difference between the IOP and the threshold value;
        in response to determining the IOP is below the threshold value and the fluid infusion is below the maximum infusion level, control the infusion pump to increase the fluid infusion in response to the changes in the IOP.

2. The system of claim 1, further comprising a sensor disposed adjacent to or at the distal end of the infusion line, the sensor configured to:
    determine, at the location adjacent to or in the eye, the sensor data relating to the IOP; and
    provide the sensor data to the controller.

3. The system of claim 1, wherein the controller is configured to control the vacuum pump by reducing a negative pressure generated by the vacuum pump in response to the IOP falling below the threshold value, or by determining a difference between the IOP and a target IOP and adjusting the vacuum pump to reduce the difference between the IOP and the target IOP.

4. The system of claim 1,
    wherein the maximum infusion level is a maximum infusion pressure or maximum infusion flow rate;
    wherein controlling the vacuum pump to reduce the fluid aspiration comprises reducing an aspiration pressure and/or aspiration flow rate; and
    wherein controlling the infusion pump to increase the fluid infusion comprises increasing the infusion pressure and/or infusion flow rate.

5. An ophthalmic surgical system, comprising:
    an infusion line having a proximal end, a distal end, and an infusion passage extending therethrough, the distal end of the infusion line being configured to enter into a vitreous chamber of an eye of a patient;
    an aspiration line having a proximal end, a distal end, and an aspiration passage extending therethrough;
    a hand piece sized and shaped for grasping by a user, the hand piece coupled to the distal end of the aspiration line; and
    a console coupled to the proximal end of the infusion line and the proximal end of the aspiration line, the console comprising:
        a vacuum pump in fluid communication with the aspiration passage, the vacuum pump configured to provide fluid aspiration from the vitreous chamber through the aspiration passage;
        an infusion chamber in fluid communication with the infusion passage;
        an infusion pump configured to provide fluid infusion from the infusion chamber to the vitreous chamber through the infusion passage; and
        a controller configured to:
            receive sensor data relating to an intraocular pressure (IOP) of the eye, the sensor data being determined at a location adjacent to or in the eye;
            control the vacuum pump to reduce the fluid aspiration in response to the IOP being below a threshold value and the fluid aspiration being above a minimum aspiration level, wherein the controller comprises a proportional-integral-derivative (PID) control used to determine a difference between the IOP and the threshold value and automatically adjust the vacuum pump to reduce the difference between the IOP and the threshold value; and
            control the infusion pump to increase the fluid infusion in response to the IOP being below the threshold value and the fluid aspiration being at or below the minimum aspiration level.

6. The system of claim 5, further comprising a sensor disposed adjacent to or at the distal end of the infusion line, the sensor being configured to:
    determine, at the location adjacent to or in the eye, the sensor data relating to the IOP; and
    provide the sensor data to the controller.

7. The system of claim 5, wherein the controller is configured to control the vacuum pump by reducing a negative pressure generated by the vacuum pump in response to the IOP falling below the threshold value, or by determining a difference between the IOP and a target IOP and adjusting the vacuum pump to reduce the difference between the IOP and the target IOP.

8. The system of claim 5,
    wherein the minimum aspiration level is a minimum aspiration pressure or a minimum aspiration flow rate;

wherein controlling the vacuum pump to reduce the fluid aspiration comprises reducing an aspiration pressure and/or an aspiration flow rate; and wherein controlling the infusion pump to increase the fluid infusion comprises increasing the infusion pressure and/or infusion flow rate.

9. A method, comprising:

receiving sensor data from a sensor adjacent to or in an eye of a patient;

monitoring for changes in an intraocular pressure (IOP) of the eye based on the sensor data;

determining whether fluid infusion to a vitreous chamber of the eye through an infusion line is below a maximum infusion level;

in response to determining the IOP is below a threshold value and the fluid infusion is below the maximum infusion level, increasing the fluid infusion; and in response to determining the IOP is below the threshold value and the fluid infusion is at or above the maximum infusion level, reducing fluid aspiration from the vitreous chamber through an aspiration line, wherein reducing the fluid aspiration comprises determining a difference between the IOP and the threshold value and using a proportional-integral-derivative (PID) to automatically adjust the vacuum pump to reduce the difference between the IOP and the threshold value.

10. The method of claim 9, wherein the reducing the fluid aspiration comprises controlling a vacuum pump in fluid communication with the aspiration line.

11. The method of claim 10, wherein the controlling the vacuum pump comprises reducing a negative pressure generated by the vacuum pump in response to the IOP falling below the threshold value, the method further comprising increasing the fluid aspiration in response to an actuation of a foot pedal.

12. The method of claim 10, wherein the controlling the vacuum pump comprises:

determining a difference between the IOP and a target IOP; and adjusting the vacuum pump to reduce the difference between the IOP and the target IOP.

13. The method of claim 9, wherein the increasing the fluid infusion comprises controlling an infusion pump associated with an infusion chamber in fluid communication with the infusion line.

14. The method of claim 9, further comprising calculating the IOP based on sensor data determined at a location adjacent to the eye, wherein the sensor data includes data for pressure, flow rate, or both.

15. The method of claim 9, wherein the maximum infusion level is a maximum infusion pressure or maximum infusion flow rate;

wherein increasing the fluid infusion comprises increasing the infusion pressure and/or infusion flow rate; and wherein reducing the fluid aspiration comprises reducing an aspiration pressure and/or aspiration flow rate.

* * * * *